(12) United States Patent
Burk et al.

(10) Patent No.: US 9,340,534 B2
(45) Date of Patent: May 17, 2016

(54) COMPOUNDS AND METHODS FOR TREATING OCULAR DISEASES

(71) Applicant: Allergan, Inc., Irvine, CA (US)

(72) Inventors: Robert M. Burk, Laguna Beach, CA (US); Todd S. Gac, Santa Ana, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/809,798

(22) Filed: Jul. 27, 2015

(65) Prior Publication Data

US 2016/0024068 A1 Jan. 28, 2016

Related U.S. Application Data

(60) Provisional application No. 62/028,976, filed on Jul. 25, 2014.

(51) Int. Cl.
*A61K 31/425* (2006.01)
*A61K 31/427* (2006.01)
*C07D 275/03* (2006.01)
*C07D 417/06* (2006.01)

(52) U.S. Cl.
CPC ............ *C07D 417/06* (2013.01); *A61K 31/425* (2013.01); *A61K 31/427* (2013.01); *C07D 275/03* (2013.01)

(58) Field of Classification Search
CPC ... C07D 275/03; A61K 31/425; A61K 31/427
USPC .......................................... 548/206; 514/372
See application file for complete search history.

(56) References Cited

U.S. PATENT DOCUMENTS 7,732,443 B2 * 6/2010 Donde .................. C07C 405/00
514/231.2

OTHER PUBLICATIONS

Berge, S., et al., Pharmaceutical Salts, J. Pharma. Sci. 1977, 66: 1-19, 1.
Ichikawa, A., et al., Molecular aspects of the structures and functions of the prostaglandin E receptors, j. Lipid Mediators & Cell Signalling 1996, 14: 83-87.
Remington's Pharmaceutical Sciences, Mack Publishing Company, Easton, Pa., 16th Edition, 1980.
Stahl, Heinrich, et al., Handbook of Pharmaceutical Salts Properties, Selection, and Use, Int'l Union of Pure & Applied Chemistry (IUPAC), 2002, 330-345.
Woodward, D.F., et al., Molecular Characterization and Ocular Hypertensive Properties of the Prostanoid EP2 Receptor, J. Ocular Pharmacology and Therapeutics 1995, 11: 447-454 (3).
Flach, Allan J., et al., Topical Prostaglandin E2 Effects on Normal Human Intraocular Pressure, Journal of Ocular Pharmacology 1988, 4: 13-18 (1).

* cited by examiner

*Primary Examiner* — Kamal Saeed
*Assistant Examiner* — Janet L Coppins
(74) *Attorney, Agent, or Firm* — Jonathan Bass

(57) ABSTRACT

Described herein are compounds of formula I

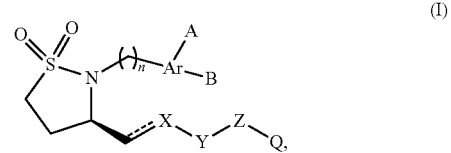

(I)

compositions and methods for the treatment of diseases affecting the eye, including glaucoma or ocular hypertension.

23 Claims, No Drawings

COMPOUNDS AND METHODS FOR TREATING OCULAR DISEASES

CROSS-REFERENCE TO RELATED APPLICATIONS

This application claims the benefit of U.S. provisional application 62/028,976 entitled "Compounds And Methods For Treating Ocular Diseases" filed on Jul. 25, 2014 with docket number 19447PROV (AP) which is incorporated herein by reference in its entirety and which serves as the basis for a priority and/or benefit claim of the present application.

FIELD OF THE INVENTION

The invention relates generally to compositions and methods for the treatment of ocular diseases and disorders, and particularly to the use of EP4 agonists for treatment of said diseases and disorders. The compounds, compositions and methods disclosed herein are particularly useful for the treatment of glaucoma and ocular hypertension.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives can be used in glaucoma management. Eicosanoids and derivatives include numerous biologically important compounds such as prostaglandins and their derivatives. Prostaglandins can be described as derivatives of prostanoic acid. Prostanoic acid has the following structural formula:

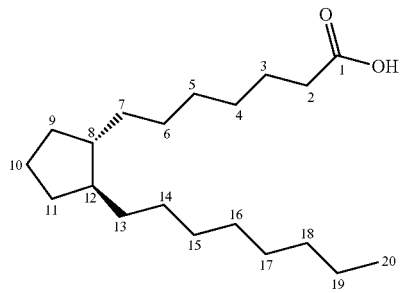 [SMILES: CCCCCCCC[C@H]1CCC[C@@H]1CCCCCCC(=O)O]

Various types of prostaglandins are classified by the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\alpha}$]. Changes in the substituents of carbons 9, 10, and 11 can often influence the activity and selectivity of these compounds at the different prostaglandin receptors. Other compounds having more remote structures from natural prostaglandins can also have activity at prostaglandin receptors.

Prostanoid EP receptors are G protein-coupled receptor that mediate the actions of prostaglandins. Four subtypes of EP receptors have been recognized in the art: EP1, EP2, EP3 and EP4. See, e.g., *J. Lipid Mediators Cell Signaling*, v. 14, 83-87 (1996). For example, EP2 binds prostaglandin E2 (PGE2) and is characterized by the longest intracellular C terminus loop when compared to other prostanoid receptors.

EP4 receptors couple to Gs and mediate elevations in cAMP concentration, although they do participate in other pathways as well. There are some redundancies in function between EP2 and EP4 receptors. For example, both receptors induce PGE2-mediated RANKL through cAMP. However, EP2 is involved in cumulus expansion in ovulation and fertilization, whereas EP4 regulates closure of the ductus arteriosus. Expression of EP4 receptors is controlled by various physiological and pathophysiological processes as these receptors participate in ovulation and fertilization, induce bone formation, protect against inflammatory bowel disease, facilitate Langerhans cell migration and maturation, and mediate joint inflammation in a model of collagen-induced arthritis, among others.

EP2 and EP4 have been associated with intraocular pressure (IOP), and ligands capable of activating these receptor subtypes have been demonstrated to lower IOP. See *J. Ocular Pharmacology*, v. 4(1), 13-18 (1988); *J. Ocular Pharmacology & Therapeutics*, v. 11(3), 447-454 (1995). Agonists of EP2 and EP4 have the potential to lower IOP and thereby treat glaucoma and other ocular diseases and disorders. Further disclosure of past studies of the relationship between lowering IOP and EP2/4 agonism is provided in WO 2010/116270, the disclosure of which is hereby incorporated by reference in its entirety.

SUMMARY OF THE INVENTION

Provided herein are compounds, compositions and methods for the treatment of diseases and disorders affecting the eye, including glaucoma or ocular hypertension.

In one embodiment of the invention, there are provided compounds of formula I:

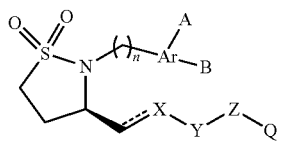

Formula I wherein:
Ar is aryl or heteroaryl, wherein each aryl or heteroaryl is optionally substituted with one or more halogens or $C_1$-$C_6$ alkyl;
n is 1, 2, 3 or 4;
X is $CH_2$, CH, S, O or $C_2$-$C_6$ alkynyl;
Y is $C_1$-$C_3$ alkyl, $C_2$-$C_6$ alkynyl or interarylene, wherein $C_1$-$C_3$ alkyl is optionally substituted by OH;
Z is interarylene, $C_1$-$C_3$ alkyl, $CH_2S$, $CH_2O$ or a bond;
Q is H, halogen, $CF_3$, $OCF_3$, $CO_2R^2$, $CH_2OR^2$, $CONR^2R^3$ or tetrazol-5-yl;
A is H, halogen, $C_1$-$C_{10}$ alkyl, $C_1$-$C_{10}$ alkyl branched alkyl, or $CO_2R^3$, wherein each $C_1$-$C_{10}$ alkyl, or $C_1$-$C_{10}$ alkyl branched alkyl contains one or more groups selected from the groups consisting of OH, OR and $NR_2$;
B is H, halogen, $C_1$-$C_{10}$ alkyl, or $C_1$-$C_{10}$ alkyl branched alkyl, wherein each $C_1$-$C_{10}$ alkyl, or $C_1$-$C_{10}$ alkyl branched alkyl contains one or more groups selected from the groups consisting of OH, OR and $NR_2$;
R is H or $C_1$-$C_6$ alkyl;
$R^1$ is H, $C_1$-$C_6$ alkyl, $CF_3$, phenyl or biphenyl;
$R^2$ is H, $C_1$-$C_6$ alkyl, $C(O)R^1$ or $SO_2R^1$; and
$R^3$ is H or $C_1$-$C_6$ alkyl.

In another embodiment, there are provided pharmaceutical compositions including at least one compound of the invention, the compound being present alone or in combination with one or more pharmaceutically acceptable excipients.

In another embodiment, there are provided compositions including at least one compound of the invention, wherein the composition is a liquid which is ophthalmically acceptable.

In another embodiment there are provided methods for the treatment of an ophthalmic disease. In some embodiments, the disease is selected from the group consisting of glaucoma, ocular hypertension, and macular degeneration. Such methods can be performed, for example, by administering to a subject in need thereof a therapeutically effective amount of at least one compound of the invention.

In another embodiment there are provided methods for reducing intraocular pressure. Such methods can be performed for example, by administering to a subject in need thereof a therapeutically effective amount of at least one compound of the invention.

In a further embodiment there are provided methods for reducing corneal thickening. Such methods can be performed for example, by administering to a subject in need thereof a therapeutically effective amount of at least one compound of the invention.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation.

As used herein, "alkyl" refers to straight or branched chain hydrocarbyl groups having from 1 up to about 20 carbon atoms. Whenever it appears herein, a numerical range, such as "1 to 10" or "$C_1$-$C_{20}$", refers to each integer in the given range; e.g., "$C_1$-$C_{20}$ alkyl" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_7$, —$CH_2OR_7$, —C(O)—, —C(O)—, —S—, —S(O)$_2$, —OC(O)—O—, wherein $R_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 20 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 20 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "alkylene" or "alkylenyl" refers to a divalent alkyl moiety. In other words, such a moiety has two points of attachment to the rest of the molecule (e.g. —$CH_2CH_2$—).

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 5 up to 14 carbon atoms and "substituted aryl" refers to aryl groups further bearing one or more substituents as set forth above.

As used herein, the terms "interaryl" and "interarylene" refer to a divalent aromatic group having in the range of 5 up to 14 carbon atoms. An exemplary interaryl group is phenylene (i.e., aromatic —$C_6H_6$—).

As used herein, "heteroaryl" refers to aromatic moieties containing one or more heteroatoms (e.g., N, O, S, or the like)

as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride, chloride, bromide or iodide" may also be referred to as "fluoro, chloro, bromo, or iodo".

Compounds

Provided herein are compounds which in some embodiments are of formula (I):

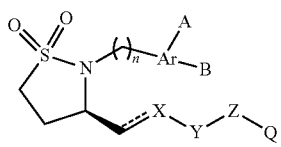

(I)

wherein:
Ar is aryl or heteroaryl, wherein each aryl or heteroaryl is optionally substituted with one or more halogens or $C_1$-$C_6$ alkyl;
n is 1, 2, 3 or 4;
X is $CH_2$, CH, S, O or $C_2$-$C_6$ alkynyl;
Y is $C_1$-$C_3$ alkyl, $C_2$-$C_6$ alkynyl or interarylene, wherein $C_1$-$C_3$ alkyl is optionally substituted by OH;
Z is interarylene, $C_1$-$C_3$ alkyl, $CH_2S$, $CH_2O$ or a bond;
Q is H, halogen, $CF_3$, $OCF_3$, $CO_2R^2$, $CH_2OR^2$, $CONR^2R^3$ or tetrazol-5-yl;
A is H, halogen, $C_1$-$C_{10}$ alkyl, $C_1$-$C_{10}$ alkyl branched alkyl, or $CO_2R^3$, wherein each $C_1$-$C_{10}$ alkyl, or $C_1$-$C_{10}$ alkyl branched alkyl contains one or more groups selected from the groups consisting of OH, OR and $NR_2$;
B is H, halogen, $C_1$-$C_{10}$ alkyl, or $C_1$-$C_{10}$ alkyl branched alkyl, wherein each $C_1$-$C_{10}$ alkyl, or $C_1$-$C_{10}$ alkyl branched alkyl contains one or more groups selected from the groups consisting of OH, OR and $NR_2$;
R is H or $C_1$-$C_6$ alkyl;
$R^1$ is H, $C_1$-$C_6$ alkyl, $CF_3$, phenyl or biphenyl;
$R^2$ is H, $C_1$-$C_6$ alkyl, $C(O)R^1$ or $SO_2R^1$; and
$R^3$ is H or $C_1$-$C_6$ alkyl.

In some embodiments of the compounds of formula I, X is CH, Y is $C_1$-$C_3$ alkyl optionally substituted by OH and Z is interarylene. In some embodiments, X is CH, Y is $C_1$-$C_3$ alkyl optionally substituted by OH and Z is phenylene. In some embodiments, X is CH, Y is $C_1$-$C_3$ alkyl substituted by OH and Z is phenylene. In some embodiments, X is CH, Y is $CH(OH)CH_2$ and Z is phenylene.

In some embodiments of the compounds of formula I, X is CH, Y is $C_1$-$C_3$ alkyl optionally substituted by OH, Z is interarylene and Q is $CF_3$. In some embodiments, X is CH, Y is $C_1$-$C_3$ alkyl optionally substituted by OH, Z is phenylene and Q is H, halogen, $CF_3$, $OCF_3$, or $CH_2OCH_3$. In some embodiments, X is CH, Y is $C_1$-$C_3$ alkyl optionally substituted by OH, Z is phenylene and Q is $CF_3$. In some embodiments, X is CH, Y is $C_1$-$C_3$ alkyl substituted by OH, Z is phenylene and Q is H, halogen, $CF_3$, $OCF_3$, or $CH_2OCH_3$. In some embodiments, X is CH, Y is $C_1$-$C_3$ alkyl substituted by OH, Z is phenylene and Q is $CF_3$. In some embodiments, X is CH, Y is $CH(OH)CH_2$, Z is phenylene and Q is H, halogen, $CF_3$, $OCF_3$, or $CH_2OCH_3$. In some embodiments, X is CH, Y is $CH(OH)CH_2$, Z is phenylene and Q is $CF_3$.

In some embodiments of the compounds of formula I, Ar is a 5 membered heteroaryl containing 1 or 2 heteroatoms selected from the group consisting of O, N and S; and n is 1, 2 or 3. In some embodiments, Ar is a 5 membered heteroaryl containing 1 or 2 heteroatoms selected from the group consisting of O, N and S; and n is 3. In some embodiments of the compounds of formula I, Ar is a 5 membered heteroaryl containing 1 or 2 heteroatoms selected from the group consisting of O, N and S; A is $CO_2R^3$; B is H and n is 1, 2 or 3. In some embodiments of the compounds of formula I, Ar is a 5 membered heteroaryl containing 1 heteroatom selected from O and S; A is $CO_2R^3$; B is H and n is 3. In some embodiments of the compounds of formula I, Ar is a 5 membered heteroaryl containing 1 heteroatom selected from O and S; A is $CO_2R^3$; $R^3$ is H; B is H and n is 3.

In some embodiments of the compounds of formula I, Ar is a 5 membered heteroaryl containing 1 or 2 heteroatoms selected from the group consisting of O, N and S; n is 1, 2 or 3; X is CH; Y is $C_1$-$C_3$ alkyl optionally substituted by OH; and Z is interarylene.

In some embodiments of the compounds of formula I, Ar is a 5 membered heteroaryl containing 1 or 2 heteroatoms selected from the group consisting of O, N and S; n is 1, 2 or 3; X is CH; Y is $C_1$-$C_3$ alkyl optionally substituted by OH; and Z is phenylene.

In some embodiments of the compounds of formula I, Ar is a 5 membered heteroaryl containing 1 or 2 heteroatoms selected from the group consisting of O, N and S; n is 1, 2 or 3; X is CH; Y is $CH(OH)CH_2$; and Z is phenylene.

In some embodiments of the compounds of formula I, Ar is a 5 membered heteroaryl containing 1 or 2 heteroatoms selected from the group consisting of O, N and S; n is 1, 2 or 3; A is $CO_2R^3$; B is H; X is CH; Y is $CH(OH)CH_2$; and Z is phenylene.

In some embodiments of the compounds of formula I, Ar is a 5 membered heteroaryl containing 1 or 2 heteroatoms selected from the group consisting of O, N and S; n is 1, 2 or 3; A is $CO_2R^3$; $R^3$ is H; B is H; X is CH; Y is $CH(OH)CH_2$; and Z is phenylene.

In some embodiments of the compounds of formula I, Ar is a 5 membered heteroaryl containing 1 heteroatom selected from the O and S; n is 1, 2 or 3; A is $CO_2R^3$; B is H; X is CH; Y is $CH(OH)CH_2$; and Z is phenylene.

In some embodiments of the compounds of formula I, Ar is a 5 membered heteroaryl containing 1 heteroatom selected from the O and S; n is 1, 2 or 3; A is $CO_2R^3$; $R^3$ is H; B is H; X is CH; Y is $CH(OH)CH_2$; and Z is phenylene.

In some embodiments of the compounds of formula I, Ar is a 5 membered heteroaryl containing 1 or 2 heteroatoms selected from the group consisting of O, N and S; n is 1, 2 or 3; A is $CO_2R^3$; $R^3$ is H; B is H; X is CH; Y is $CH(OH)CH_2$; Z is phenylene; and Q is H, halogen, $CF_3$, $OCF_3$, or $CH_2OCH_3$.

In some embodiments of the compounds of formula I, Ar is a 5 membered heteroaryl containing 1 or 2 heteroatoms selected from the group consisting of O, N and S; n is 1, 2 or 3; A is $CO_2R^3$; $R^3$ is H; B is H; X is CH; Y is $CH(OH)CH_2$; Z is phenylene; and Q is $CF_3$, In some embodiments of the compounds of formula I, Ar is a 5 membered heteroaryl containing 1 heteroatom selected from the O and S; n is 1, 2 or 3; A is CO$_2$R$^3$; B is H; X is CH; Y is CH(OH)CH$_2$; Z is phenylene; and Q is H, halogen, CF$_3$, OCF$_3$, or CH$_2$OCH$_3$.

In some embodiments of the compounds of formula I, Ar is a 5 membered heteroaryl containing 1 heteroatom selected from the O and S; n is 1, 2 or 3; A is CO$_2$R$^3$; B is H; X is CH; Y is CH(OH)CH$_2$; Z is phenylene; and Q is CF$_3$.

In some embodiments of the compounds of formula I, Ar is a 5 membered heteroaryl containing 1 heteroatom selected from the O and S; n is 1, 2 or 3; A is CO$_2$R$^3$; R$^3$ is H; B is H; X is CH; Y is CH(OH)CH$_2$; Z is phenylene; and Q is H, halogen, CF$_3$, OCF$_3$, or CH$_2$OCH$_3$.

In some embodiments of the compounds of formula I, Ar is a 5 membered heteroaryl containing 1 heteroatom selected from the O and S; n is 1, 2 or 3; A is CO$_2$R$^3$; R$^3$ is H; B is H; X is CH; Y is CH(OH)CH$_2$; Z is phenylene; and Q is CF$_3$.

In one embodiment, the compound is of the formula:

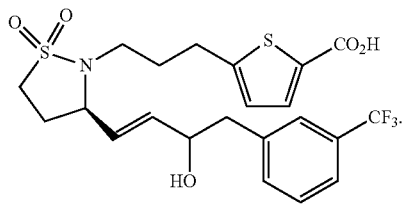

In another embodiment, the compound is of the formula:

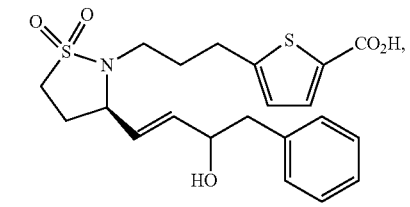

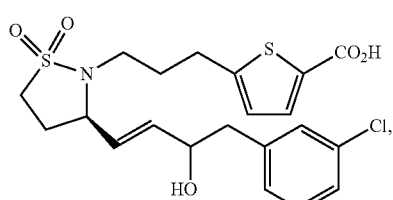

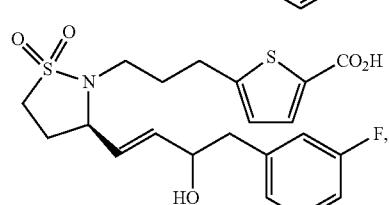

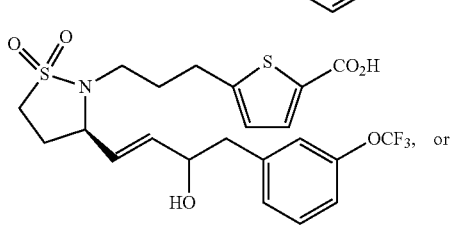

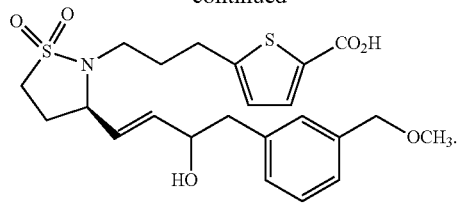

In some embodiments, the compounds provided herein may exist in salt forms, such that the corresponding anions or cations may form a pharmaceutically acceptable salt, such as for example, hydrochloride, hydrobromide, hydroiodide, sulfate, bisulfate, phosphate or acid phosphate, acetate, maleate, fumarate, oxalate, lactate, tartrate, citrate, gluconate, saccharate, p-toluenesulfonate salts, or other anionic counter-ions; or sodium, potassium, ammonium or other cationic counter-ions.

A "pharmaceutically acceptable salt" includes any salt that retains the activity of the parent compound and is acceptable for pharmaceutical use. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Exemplary ions are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring. (See, e.g., *Handbook of Pharmaceutical Salts*, P. Heinrich Stahl & Camille G. Wermuth (Eds), Verlag; *Helvetica Chimica Acta*-Zürich, 2002, 329-345.) The term "pharmaceutically acceptable salt" is also meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66:1-19). Certain specific compounds of the present invention may contain both basic and acidic functionalities that allow the compounds to be converted into either base or acid addition salts.

Compounds of the invention may be synthesized in a variety of ways known to those skilled in the art. Schemes 1 and 2 set forth below set forth exemplary synthetic routes to certain compounds of the invention.

Pharmaceutical Compositions and Methods of Treatment

The disclosed compounds can be administered as part of a composition. As used herein, "formulation" and "composition" may be used interchangeably and refer to a combination of elements that is presented together for a given purpose. Such terms are well known to those of ordinary skill in the art.

As used herein, "carrier," "inert carrier," and "acceptable carrier" may be used interchangeably and refer to a carrier which may be combined with the presently disclosed compounds in order to provide a desired composition. Those of ordinary skill in the art will recognize a number of carriers that are well known for making specific pharmaceutical compositions.

As used herein, the term "therapeutically effective amount" means the amount of the pharmaceutical or cosmetic composition that will elicit the biological, medical, or cosmetic response of a subject in need thereof that is being sought by the researcher, veterinarian, medical doctor or other clinician. In some embodiments, the subject in need thereof is a mammal. In certain embodiments, the mammal is human. Effective amounts of the compound may be determined by one of ordinary skill in the art but will vary depending on the compound employed, frequency of application and desired result, and will generally range from about 0.0000001% to about 50%, by weight, of the composition, preferably from about 0.001% to about 50%, by weight, of total composition, more preferably from about 0.001% to about 30%, by weight of the composition. In certain embodiments, the compound is about 0.004% by weight of the composition.

The amount of the subject compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the subject compounds may be in the range of about 0.5 or about 1 to about 100 mg/kg/day.

The compounds described herein may be administered at least in the minimum dose necessary to achieve the desired therapeutic effect. Generally, such doses will be in the range of about 1 mg/day to about 1000 mg/day; more preferably in the range of about 10 mg/day to about 500 mg/day. In another example embodiment, the compound or compounds may be present in a composition or formulation in a range of about 0.0001 mg/kg/day to about 100 mg/kg/day or about 0.01 mg/kg/day to about 100 mg/kg/day. However, the actual amount of the compound to be administered in any given case will be determined by a physician taking into account the relevant circumstances, such as the age and weight of a patient, patient's general physical condition, severity of the skin blemish, and route of administration. In some instances, dosing is evaluated on a case-by-case basis.

Additionally, compositions may be designed to delay release of the compound over a given period of time, or to carefully control the amount of compound released at a given time during the course of treatment.

The pH of the disclosed compositions can be about 3 to about 8.0, or about 6.5 to about 7.5. In certain embodiments, the pH of the formulation is about 7.0 to about 7.4 or about 7.1 to about 7.3.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Liquid pharmaceutically administrable dosage forms can, for example, comprise a solution or suspension of one or more of the subject compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. The composition of the formulation to be administered, in any event, contains a quantity of one or more of the subject compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

An ophthalmically acceptable pharmaceutical composition is one that can be administered topically to the eye of a subject in need thereof. Comfort to the subject being administered the composition should be maximized, but other considerations, such as drug stability, may necessitate a pharmaceutical composition that provides less than optimal comfort. In such a case, the composition should be formulated such that it is tolerable to a subject being administered the composition topically.

The pharmaceutical composition can be administered topically in the form of solutions or suspensions, ointments, gels, creams, etc. A "pharmaceutically acceptable excipient" is one that is compatible with the active ingredient of the composition and not harmful to the subject being administered the pharmaceutical composition. Solutions for ophthalmic application are often prepared using physiological saline as a major vehicle. Other vehicles include polyvinyl alcohol, povidone, hydroxypropyl methyl cellulose, poloxamers, carboxymethyl cellulose, hydroxyethyl cellulose, and purified water. Examples of useful excipients also include preservatives, buffers, other pH adjustors, tonicity adjustors, surfactants, antioxidants, and chelating agents.

Useful preservatives include benzalkonium chloride, chlorobutanol, thimerosal, phenylmercuric acetate and phenylmercuric nitrate. Examples of buffers include phosphate, borate, sulfate, acetate, and citrate buffers. Acids or bases may be used to adjust the pH of the compositions as needed. Examples of tonicity agents include glycerin, mannitol, sodium chloride and potassium chloride. Useful surfactants include, for example, Tween 80. Examples of ophthalmically acceptable antioxidants include sodium metabisulfite, sodium thiosulfate, acetylcysteine, butylated hydroxyanisole and butylated hydroxytoluene. A useful chelating agent is edentate disodium.

Mixtures of two or more of any suitable excipients may be used. The aforementioned examples are not intended to limit the scope of the invention in any way. In some embodiments, the ingredients are used in the following amounts:

| Ingredient | Amount (Weight/Volume Percentage) |
| --- | --- |
| active ingredient | About 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

A therapeutically effective amount of at least one compound of the invention in the pharmaceutical composition disclosed herein is an amount useful to observe a therapeutic effect as compared to a placebo composition that, except for the absence of a compound of the invention, is otherwise identical to the pharmaceutical composition. The amount of at least one compound of the invention to administer depends on factors such as the intended therapeutic effects, the specific mammal in need thereof, the severity and nature of the mammal's condition, the manner of administration, the potency and pharmacodynamics of the particular compound, and the judgment of the prescribing physician. The therapeutically effective dosage of at least one compound of the invention is preferably in the range of about 0.5 or about 1 to about 100 mg/kg/day.

Also, an ophthalmically acceptable pharmaceutical composition should be packaged for single use, or contain a preservative to prevent contamination over multiple uses.

Aside from topical application to treat diseases affecting the eye including glaucoma, pharmaceutical compositions containing at least one compound of the invention can also be administered periocularly, intraocularly, or by other effective means available in the art.

Persons skilled in the art would readily understand that a drug containing one or more of the compounds disclosed herein can be confected as a powder, pill, tablet or the like, or as a solution, emulsion, suspension, aerosol, syrup or elixir suitable for oral or parenteral administration or inhalation. For solid dosage forms or medicaments, non-toxic solid excipients for admixture with compounds disclosed herein include, but are not limited to, pharmaceutical grades of mannitol, lactose, starch, magnesium stearate, sodium saccharin, polyalkylene glycols, talcum, cellulose, glucose, sucrose, and magnesium carbonate. The solid dosage forms may be coated by a material such as glyceryl monostearate or glyceryl distearate, which is utilized in known techniques to delay disintegration and absorption in the gastrointestinal tract for the purpose of providing a sustained action over a longer period. Solid dosage forms may also be coated by the techniques described in U.S. Pat. Nos. 4,256,108, 4,166,452 and 4,265,874 to form osmotic therapeutic tablets for control release.

Pharmaceutically administrable liquid dosage forms can, for example, comprise a solution or suspension of at least one of the compounds disclosed herein and optional pharmaceutical adjutants in a carrier, such as water, saline, aqueous dextrose, glycerol, ethanol and the like. The liquid dosage forms may also contain nontoxic auxiliary substances such as wetting or emulsifying agents, pH buffering agents and the like. Examples of such auxiliary agents include sodium acetate, sorbitan monolaurate, triethanolamine, sodium acetate, triethanolamine oleate, etc. Methods for preparing such dosage forms are well-known to persons skilled in the art (see, for example, *Remington's Pharmaceutical Sciences*, Mack Publishing Company, Easton, Pa., 16$^{th}$ Edition, 1980).

For the treatment of diseases affecting the eye, including glaucoma, the compounds provided herein may be administered topically, perioculary, intraocularly, or by any other effective means known in the art. The compounds may be administered as ophthalmic solutions in combination with ophthalmically acceptable carriers and diluents. Such ophthalmic solutions may be prepared for administration in containers, such as eye droppers—either as unit dosage forms or multi dose containers.

The compositions may be administered between 1 and 7 days a week, for a period of time necessary to achieve the desired results, which may be several days to several months. The compositions can be administered once or several times (2, 3, 4, or more times) a day depending on the desired effect. In certain embodiments, the compositions can be administered every 1, 2, 3, 4, 5, 6, or 7 days. In another embodiment, the compositions can be administered one or more times every 1, 2, 3, or 4 weeks. The administration can be on a monthly or bi-monthly basis. Further, the compositions can be administered for 1, 2, 3, 6, 9, or 12 months or more. In certain embodiments, the compositions can be administered on an ongoing basis to maintain a desired result.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof; and $\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like or pharmaceutically acceptable salts or prodrugs thereof;

Cholinergic Agonists Including:

direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as Ca$^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UF-021, chloprostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

The following schemes illustrate exemplary methods for the preparation of compounds of the invention. One skilled in the art may modify these methods to arrive at other compounds within the scope of the invention, or use alternative methods known in the art.

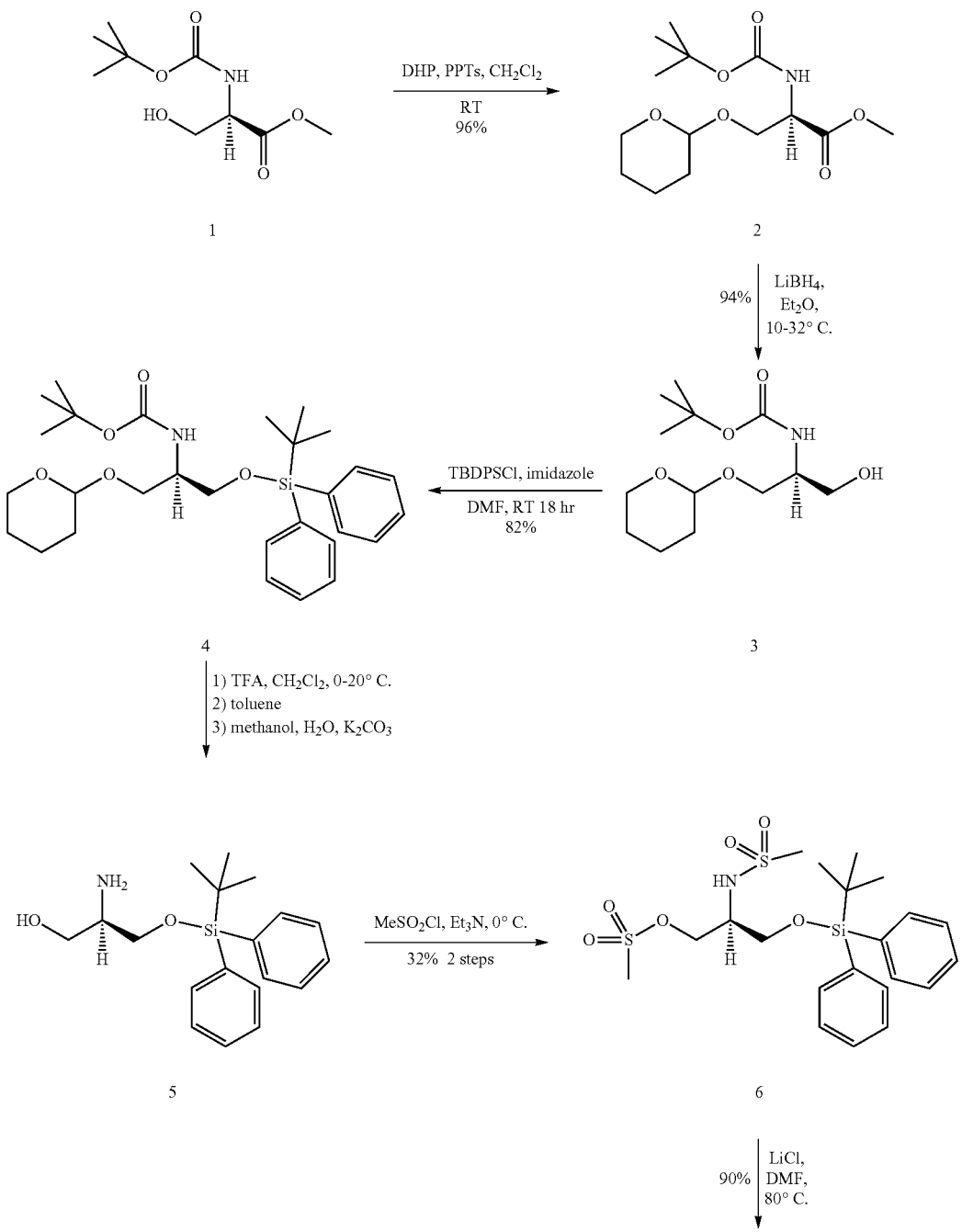

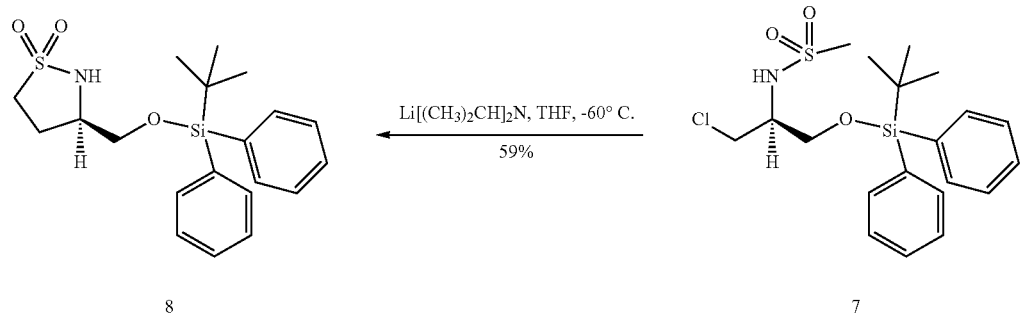
Scheme 2
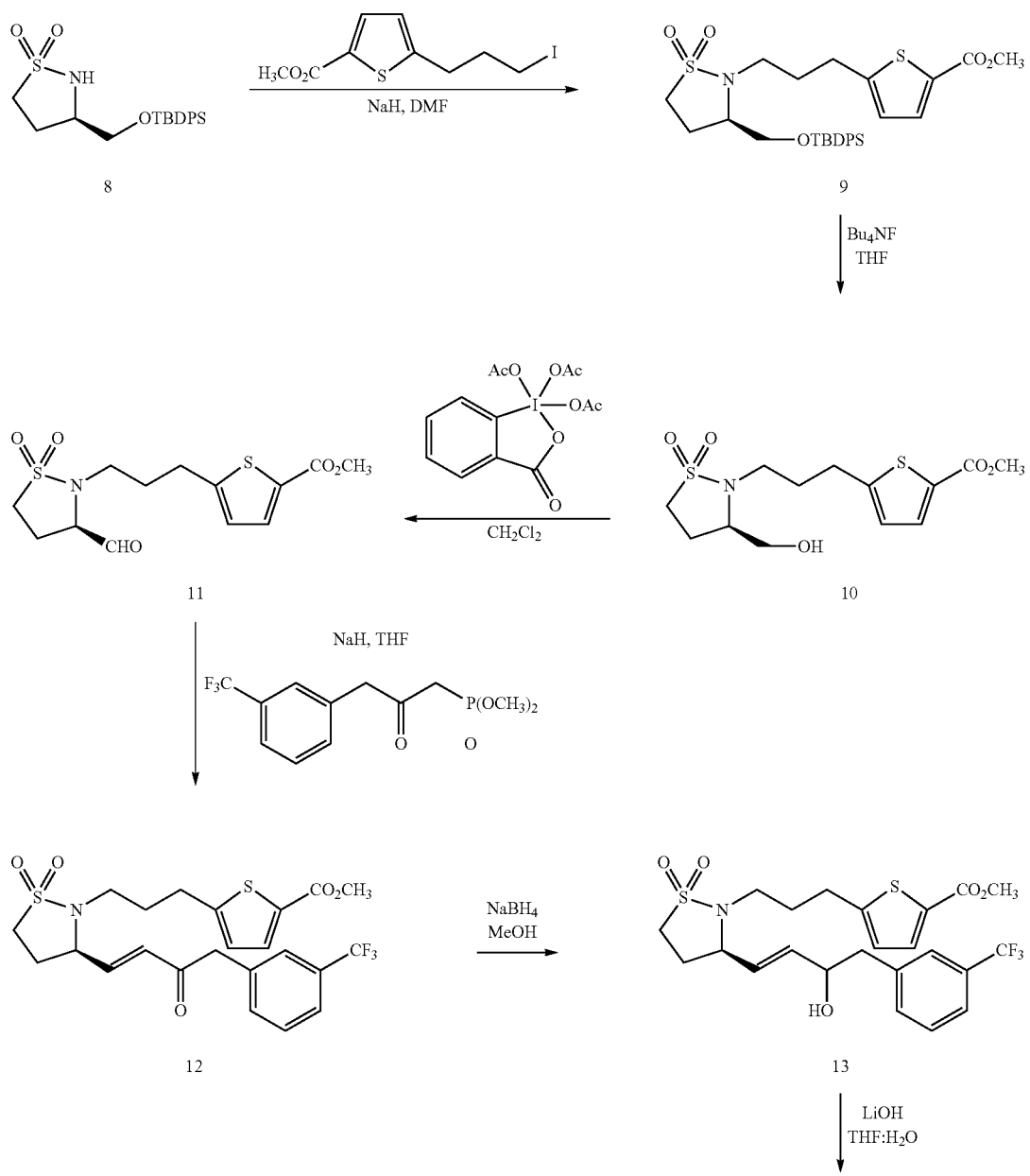

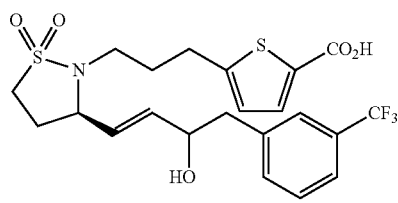

14

Examples

The examples provided herein are intended only to illustrate the invention and should in no way be construed as limiting the invention. The following synthetic examples are generally applicable for the preparation of compounds within the scope of formula (I), include those specifically described above, as provided herein.

Synthetic Procedures (2R)-Methyl 2-((tert-butoxycarbonyl)amino)-3-((tetrahydro-2H-pyran-2-yl)oxy)propanoate (2)

To a 2 L three neck flask fitted with a magnetic stirbar, under argon, was added $CH_2Cl_2$ (500 mL), PPTs (pyridinium-p-toluene sulfonate) (2 g, 0.008 mol). After dissolving the PPTs by stirring, N-(tert-butoxycarbonyl)-D-serine methyl ester 1 (97.9 g, 0.446 mol) was added to give a clear yellow solution. DHP (3,4-dihydro-2H-pyran) (105 mL, 1.16 mol) was added in one portion. The clear yellow solution was stirred at room temperature over 60 hr to give a slightly cloudy yellow mixture. The mixture was evaporated to give an off-white solid. Ethyl acetate (650 mL) was added to the residue and stirred for 20 minutes to dissolve. The solution was washed with 1.2M HCl (1×500 mL) to pH 4, sat. $NaHCO_3$ (1×600 mL plus 1λ300 mL) to pH 7, brine (1×500 mL), dried over $MgSO_4$ (20 g), filtered and concentrated under reduced pressure to give 129 g (96%) of product 2 as a waxy white solid. $^1H$ NMR (60 MHz, $CDCl_3$) δ 5.2-5.7 (br m, 1H), 3.4-4.8 (m, 9H), 1.4-1.8 (m, 15H).

tert-Butyl ((2S)-1-hydroxy-3-((tetrahydro-2H-pyran-2-yl)oxy)propan-2-yl)carbamate (3)

To a 3 L three neck flask fitted with a thermometer, magnetic stirrer, under argon was added 2 (128 g, 0.42 mol) in diethyl ether (1.5 L). A clear yellow solution formed after one hour of stirring at room temperature. The solution was cooled to 10° C. with an ice/water bath. Lithium borohydride (9.3 g, 0.42 mol) was added in three portions over 30 minutes to keep the temperature below 18° C. The reaction mixture was warmed to 32° C. and was complete after 60 min by TLC (EtOAc:Hexanes; 3:7, anisaldehyde dip reagent). The reaction mixture was transferred to a 4 L flask and stirred vigorously while 1M NaOH (350 mL) was added slowly to pH 11 and stirred an additional 30 min. Ethyl acetate (500 mL) was added to the mixture and stirred 5 min. The layers were separated. The organic layer was washed with brine (1×600 mL) and dried over granular $Na_2SO_4$ (100 g) for 15 min. The mixture was filtered and concentrated under reduced pressure overnight to 109 g (94%) of product 3 as a waxy white crystalline solid. $^1H$ NMR (60 MHz, $CDCl_3$) δ 5.0-5.3 (br m, 1H), 3.2-4.6 (m, 8H), 2.4-3.0 (m, 1H), 1.3-1.7 (m, 15H).

tert-Butyl ((2R)-1-((tert-butyldiphenylsilyl)oxy)-3-((tetrahydro-2H-pyran-2-yl)oxy)propan-2-yl)carbamate (4)

To a 5 L three neck flask fitted with a thermometer, mechanical stirrer, under argon was added 3 (108 g, 0.39 mol) and DMF (700 mL). To the light yellow solution was added imidazole (53 g, 0.78 mol) and TBDPSCl (tert-butyldiphenylchlorosilane) (150 mL, 0.58 mol). The solution turned cloudy and colorless. After stirring 18 hours the reaction was shown to be complete by TLC (EtOAc:hexanes; 3:7, anisaldehyde dip reagent). The clear yellow solution was concentrated under reduced pressure to a yellow residue (415 g). The residue was dissolved in diethyl ether (2 L) in a 4 L flask with a mechanical stirrer. To this solution was added 1.2M HCl (300 mL) to pH 3-4. The solution was stirred for 10 min. The layers were separated and the organic layer was washed with sat. $NaHCO_3$ (300 mL) to pH 7 and brine (400 mL). The organic layer was dried over $MgSO_4$ (60 g), filtered and concentrated under reduced pressure to 248 g of an oil. The oil was flashed chromatographed in portions over flash silica as follows. The oil (60 g) was flash chromatographed over flash silica gel (440 g) with anhydrous $Na_2SO_4$ (100 g) on top of the column packed with hexanes. Fractions of 500 mL were collected. Fractions 1-2 were eluted with hexanes, 3-10 with 4% ethyl acetate in hexanes, 11-18 with 10% ethyl acetate in hexanes. Fractions were monitored by TLC (EtOAc:hexanes; 2:8, anisaldehyde dip reagent) and HPLC. Fractions 9-18 were combined and concentrated under reduced pressure to give 37 g (18%) of product 4 as a viscous colorless oil. HPLC analysis showed a purity of 98%. The total weight of product 4 after purifications was 164 g (82%). $^1H$ NMR (60 MHz, $CDCl_3$) δ 7.0-7.7 (m, 10H), 3.2-5.2 (m, 9H), 1.0-2.0 (m, 24H).

(R)-2-Amino-3-((tert-butyldiphenylsilyl)oxy)propan-1-ol (5)

To a 2 L three neck flask fitted with a thermometer, mechanical stirrer, under argon was added 4 (46 g, 0.089 mol) and $CH_2Cl_2$ (1 L). The clear colorless solution was cooled to 0° C. with an ice/methanol bath. The TFA (132 g, 1.16 mol) was added in one portion. After stirring for 3 hr 30 min and allowing to warm to 20° C., the reaction was complete by HPLC. The reddish brown solution was concentrated under reduced pressure. Toluene (1×100 mL and 1×50 mL) was added to the residue and twice concentrated to remove excess TFA. To the resulting red oil was added methanol (600 mL) and water (200 mL). Potassium carbonate (110 g) was added to the resulting solution and stirred vigorously for 2 hr and 15 min. Dichloromethane (1.2 L) was added to the stirring solution. The aqueous layer was separated and extracted with $CH_2Cl_2$ (1 L). The organic layers were combined and dried over $MgSO_4$ (20 g), filtered and concentrated under reduced pressure to 44 g of a cloudy orange oil. The oil was dissolved in $CH_2Cl_2$ (200 mL) and dried again over $MgSO_4$ (6 g), filtered and concentrated under reduced pressure to 39 g of product 5 as an orange oil. HPLC analysis showed a purity of 54% at a retention time of 2.8 min at 215 nm (Hewlett Packard series 1100 HPLC instrument, using an Alltech Alltima column ($C_{18}$, 5μ, 250×4.6 mm), with a flow rate of 1.0 mL/min at 40° C., conditions 0:5:95; Water:Al:MeOH, Al consists of 700 mL of water, 300 mL of methanol, and 3 mL of triethylamine adjusted to pH 3.4 with phosphoric acid). There were three major impurities by HPLC at retention times of 3.1 min (21%), 3.4 min (15%) and 3.8 min (9%). The product 5 was carried on without further purification $^1$H NMR (60 MHz, $CDCl_3$) δ 7.0-7.7 (m, 10H), 3.4-3.9 (m, 5H), 1.8-2.2 (br s, 1H), 1.1 (s, 9H).

(S)-3-((tert-Butyldiphenylsilyl)oxy)-2-(methylsulfonamido)propyl-methane-sulfonate (6)

To a 2 L three neck flask fitted with a thermometer, mechanical stirrer, addition funnel, under argon was added the crude amino alcohol 5 (75 g, 0.23 mol) dissolved in dry THF (800 mL). The solution was cooled to −10° C. with an ice/methanol bath. Triethylamine (56 g, 0.55 mol) was added in one portion. Methanesulfonyl chloride (58 g, 0.51 mol) dissolved in THF (60 mL) was added dropwise to keep the temperature below 0° C. Additional triethylamine (10 g, 0.10 mol) and methanesulfonyl chloride (10 g, 0.08 mol) were added keeping the temperature below 0° C. The reaction was complete after 75 min by HPLC. tert-Butyl methyl ether (200 mL) was added to the reaction mixture and stirred for 10 min to precipitate out triethylamine hydrochloride. The mixture was filtered through glass fiber paper and the filter cake pressed and washed with THF (2×10 mL). The filtrate was concentrated at reduced pressure to an orange oily residue. This residue was dissolved in $CH_2Cl_2$ (700 mL) and washed with sat. $NaHCO_3$ (450 mL) and brine (450 mL). The organic layer was dried over $MgSO_4$ (10 g), filtered and concentrated under reduced pressure to 102 g of red oil. The oil (50 g) was flash chromatographed over flash silica gel (450 g) with anhydrous $Na_2SO_4$ (100 g) on top of the column packed with hexanes. Fractions of 500 mL were collected. Fractions 1-4 were eluted with 10% ethyl acetate in hexanes, 5-8 with 20% ethyl acetate in hexanes, 9-12 with 40% ethyl acetate in hexanes, 13-16 with 60% ethyl acetate in hexanes. Fractions were monitored by TLC (EtOAc:hexanes; 1:1, anisaldehyde dip reagent) and HPLC. Fractions 7-14 were combined and concentrated under reduced pressure to give 13.9 g of product 6 as a viscous yellow oil. HPLC analysis showed a purity of 93%. The remaining red oil and impure fractions from the previous column were combined and flash chromatographed similarly to give 35 g of product with an HPLC purity of 95%. The total weight of 6 after purifications as a viscous yellow oil was 48.9 g. The overall yield for the previous 2 steps is 32%. $^1$H NMR (300 MHz, $CDCl_3$) δ 7.3-7.7 (m, 10H), 4.6-4.8 (m, 1H), 4.3-4.5 (m, 2H), 3.7-3.9 (m, 3H), 3.0 (s, 3H), 2.9 (s, 3H), 1.1 (s, 9H).

(S)—N-(1-((tert-butyldiphenylsilyl)oxy)-3-chloropropan-2-yl)methane-sulfonamide (7)

To a 250 mL three neck flask fitted with a thermometer, condenser, stirbar, under argon was added the bis-methanesulfonyl derivative 6 (44 g, 0.091 mol) dissolved in DMF (200 mL). Lithium chloride (5.8 g, 0.136 mol) was added in one portion. The reaction mixture was heated to 80° C. with an oil bath. After 90 min the reaction was allowed to cool to room temperature and diluted with 50% ethyl acetate in hexanes (880 mL). The layers were separated and the organic layer was washed with water (2×550 mL) and brine (550 mL). The organic layer was dried over $MgSO_4$, filtered and concentrated under reduced pressure to 35 g (90%) of the chlorosulfonamide 7 as a yellow viscous oil. HPLC analysis showed a purity of 95%. $^1$H NMR (300 MHz, $CDCl_3$) δ 7.3-7.7 (m, 10H), 4.6-4.8 (m, 1H), 3.6-4.0 (m, 5H), 2.9 (s, 3H), 1.1 (s, 9H).

(R)-3-(((tert-Butyldiphenylsilyl)oxy)methyl)isothiazolidine 1,1-dioxide (8)

To a 1 L three neck flask fitted with a thermometer, mechanical stirrer, addition funnel, under argon was added the chlorosulfonamide 7 (35 g, 0.082 mol) dissolved in THF (500 mL). The reaction mixture was cooled to −62° C. LDA (Lithium diisopropylamide, 2.0 M in heptanes/THF/ethylbenzene, 193 mL, 0.385 mol) was added drop wise over 90 min. The reaction mixture warmed to −30° C. The cooling bath was turned off and 1M HCl (1 L) was added slowly initially, then the solution was transferred to a reparatory funnel where the remaining HCl was added to pH 2. The layers were separated and the aqueous layer was extracted with ethyl acetate (400 mL). The organic layers were combined and washed with sat. $NaHCO_3$ (250 mL) and brine (250 mL). The organic layer was dried over $MgSO_4$ (10 g) filtered and concentrated under reduced pressure to 37.2 g of an orange oil. The oil was flash chromatographed over flash silica gel (400 g) with anhydrous $Na_2SO_4$ (100 g) on top of the column packed with hexanes. Fractions of 500 mL were collected. Fractions 1-17 were eluted with pure hexanes up to 12% ethyl acetate in hexanes, 18-26 with 20% ethyl acetate in hexanes, 27-30 with 50% ethyl acetate in hexanes. Fractions were monitored by TLC (EtOAc:hexanes; 1:1) and HPLC. Fractions 21-29 were combined and concentrated under reduced pressure and further dried submersed in a warm water bath at 50° C. under high vacuum over night to give 18.8 g (59%) of the final product 8 as a viscous honey colored oil. HPLC analysis showed a purity of 95%. $^1$H NMR (300 MHz, $CDCl_3$) δ 7.3-7.7 (m, 10H), 4.4-4.6 (br s, 1H), 3.6-3.9 (m, 3H), 3.2 (m, 2H), 2.1-2.6 (m, 2H), 1.1 (s, 9H). This batch was sent as lot #07-OC-FP-019.

(R)-Methyl 5-(3-(3-(((tert-butyldiphenylsilyl)oxy) methyl)-1,1-dioxido-isothiazolidin-2-yl)propyl) thiophene-2-carboxylate (9)

To a mixture of sodium hydride (37 mg, 1.54 mmol) in DMF (3.0 mL) cooled to 0° C. was added dioxide 8 (554 mg, 1.42 mmol). After 0.5 h a solution methyl 5-(3-iodopropyl) thiophene-2-carboxylate (485 mg, 1.56 mmol) in DMF (4.5 mL). The reaction was allowed to warm to room temperature on its own accord and stirred for 16 h. The reaction was quenched with saturated aqueous ammonium chloride and extracted with EtOAc. The organic portion was washed with brine, dried ($MgSO_4$), filtered and concentrated in vacuo. Purification of the residue by flash column chromatography (silica gel, 20% EtOAc/hex) afforded 751 mg (91%) of ester 9.

(R)-Methyl 5-(3-(3-(hydroxymethyl)-1,1-dioxido-isothiazolidin-2-yl)-propyl)-thiophene-2-carboxylate (10)

Tetrabutylammonium fluoride (1.95 mL of a 1.0M solution in THF, 1.95 mmol) was added to a solution of the silyl ether 9 (751 mg, 1.29 mmol) in THF (3.0 mL). After stirring for 16 h the reaction was diluted with EtOAc and washed with water followed by brine. The organic portion was dried ($MgSO_4$), filtered and concentrated in vacuo. Purification of the residue by flash column chromatography (silica gel, 20% EtOAc/hex followed by 40% EtOAc/hex) afforded 317 mg (73%) of alcohol 10.

(R)-Methyl 5-(3-(3-formyl-1,1-dioxidoisothiazolidin-2-yl)propyl)thio-phene-2-carboxylate (11)

1,1,1-Tris(acetyloxy)-1,1-dihydro-1,2-benziodoxol-3-(1H)-one (476 mg, 1.00 mmol) was added to a solution of the alcohol 10 (312 mg, 0.94 mmol) in $CH_2Cl_2$ (3.0 mL) at 23° C. The reaction was stirred for 16 h, filtered through celite and concentrated in vacuo. The residue was purified by flash column chromatography (silica gel, 10% EtOAc/hex) afforded 155 mg (50%) of aldehyde 11.

(R,E)-Methyl 5-(3-(1,1-dioxido-3-(3-oxo-4-(3-(trifluoromethyl)phenyl)-but-1-en-1-yl)isothiazolidin-2-yl)propyl)thiophene-2-carboxylate (12)

To a suspension of sodium hydride (12 mg, 0.5 mmol) in THF (1.0 mL) cooled to 0° C. was added a solution of dimethyl (2-oxo-3-(3-(trifluoromethyl)phenyl)propyl)-phosphonate (160 mg, 0.52 mmol) in THF (2.0 mL). After 15 min a solution of the aldehyde 11 (155 mg, 0.47 mmol) in THF (2.0 mL) was added. The reaction was allowed to warm room temperature and stirred for 16 h. The reaction was quenched with saturated aqueous ammonium chloride and extracted with EtOAc. The organic portion was washed with brine, dried ($MgSO_4$), filtered and concentrated in vacuo. Purification of the residue by flash column chromatography (silica gel, 40% EtOAc/hex) afforded 240 mg (99%) of enone 12.

Methyl 5-(3-((3R)-3-((E)-3-hydroxy-4-(3-(trifluoromethyl)phenyl)but-1-en-1-yl)-1,1-dioxidoisothiazolidin-2-yl)propyl)thiophene-2-carboxylate (13)

Sodium tetrahydridoborate (22 mg, 0.58 mmol) was added to a solution of the enone 12 (268 mg, 0.52 mmol) in MeOH (3.0 mL) at 0° C. The reaction was gradually allowed to warm to room temperature and stirred an additional 5 h. The solvent was removed in vacuo. The residue was partitioned between EtOAc and saturated aqueous ammonium chloride. The organic portion was separated then washed with brine, dried ($MgSO_4$), filtered and concentrated in vacuo. Purification of the residue by flash column chromatography (silica gel, 3:1 EtOAc/hex) afforded 24 mg (9%) of pure alcohol 13.

5-(3-((3R)-3-((E)-3-Hydroxy-4-(3-(trifluoromethyl) phenyl)but-1-en-1-yl)-1,1-dioxidoisothiazolidin-2-yl)propyl)thiophene-2-carboxylic acid (14)

Lithium hydroxide (0.25 mL of a 0.5N solution in H2O, 0.125 mmol) was added to a solution of the ester 13 (25 mg, 0.048 mmol) in THF (1.0 mL) at 23° C. The reaction mixture was stirred for 16 h, acidified with acetic acid and extracted with EtOAc. The organic portion was washed with brine, dried ($Na_2SO_4$), filtered and concentrated in vacuo. Purification of the residue by flash column chromatography (silica gel, 10% $MeOH/CH_2Cl_2$) afforded 10 mg (41%) of pure carboxylic acid 14.

Biological Assays

Binding Data ($K_i$)

Competition binding experiments were performed in a medium containing Hank's balanced salt solution, Hepes 20 mM, pH 7.3, membranes (~60 μg protein) or $2 \times 10^5$ cells from HEK 293 cells stably expressing human EP2 receptors, [$^3$H] PGE2 (10 nM) and various concentrations of test compounds in a total volume of 300 μl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3). Non-specific binding was estimated in the presence of excess unlabeled PGE2 (10 μM). Binding data fitted to the binding model for a single class of binding sites, using nonlinear regression analysis. $IC_{50}$ values thus obtained were converted to Ki using the equation of $Ki=(IC_{50}/(1+[L]/K_D)$ where [L] represents PGE2 concentration (10 nM) and $K_D$ the dissociation constant for [$^3$H]PGE2 at human EP2 receptors (40 nM).

Radioligand Binding

Cells Stably Expressing $EP_1$, EP2, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl $PGF_{2\alpha}$ (5 nM) were performed in a 100 μl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H—] $PGE_2$ (specific activity 180 Ci mmol) was used as the radioligand for EP receptors. [$^3$H] 17-phenyl $PGF_{2\alpha}$ was employed for FP receptor binding studies. Binding studies employing $EP_1$, $EP_2$, $EP_4$ and FP receptors were performed in duplicate in at least three separate experiments. A 200 μl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-$PGE_2$, or 5 nM [$^3$H] 17-phenyl $PGF_{2\alpha}$ and non-specific binding determined with $10^{-5}$M of unlabeled $PGE_2$, or 17-phenyl $PGF_{2\alpha}$, according to receptor subtype studied.

| Compound | EP2 | | EP4 | |
| --- | --- | --- | --- | --- |
| | cAMP EC50 (nM) | Binding EC50 (nM) | cAMP EC50 (nM) | Binding EC50 (nM) |
| 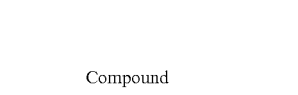 14 | 38 | 96 | 1 | 53 |

In Vivo Testing—Intraocular Pressure (IOP)

Intraocular pressure studies in dogs involved pneumatonometry performed in conscious, Beagle dogs of both sexes (10-15 kg). The animals remained conscious throughout the study and were gently restrained by hand. Drugs were administered topically to one eye as a 25 μL volume drop, the other eye received 25 μL vehicle (0.1% polysorbate 80: 10 mM TRIS) as a control. Proparacaine (0.1%) was used for corneal anesthesia during tonometry. Intraocular pressure was determined just before drug administration and at 2, 4 and 6 hr thereafter on each day of the 5 day study. Drug was administered immediately after the first IOP reading.

Ocular Surface Hyperemia

Ocular surface hyperemia was visually assessed and scored according to a system typically used clinically.

| Hyperimia Score | Assigned Value |
| --- | --- |
| <1 trace | 0.5 |
| 1 mild | 1 |
| moderate | 2 |
| severe | 3 |

Ocular surface hyperemia was evaluated at the same time points as intraocular pressure measurement. It should be noted that untreated dog eyes frequently have a pink/red tone. Thus, values of trace or even mild are not necessarily out of the normal range. Similar tests were used to determine ocular surface hyperemia on monkeys.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated. To the extent that any recitations in the incorporated references conflict with any recitations herein, the recitations herein will control.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A compound of formula I:

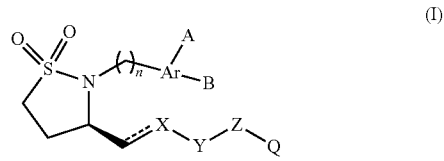

or a pharmaceutically acceptable salt thereof, wherein:
Ar is aryl or heteroaryl, wherein each aryl or heteroaryl is optionally substituted with one or more halogens or $C_1$-$C_6$ alkyl;
n is 1, 2, 3 or 4;
X is $CH_2$, CH, S, O or $C_2$-$C_6$ alkynyl;
Y is $C_1$-$C_3$ alkyl, $C_2$-$C_6$ alkynyl or interarylene, wherein $C_1$-$C_3$ alkyl is optionally substituted by OH;
Z is interarylene, $C_1$-$C_3$ alkyl, $CH_2S$, $CH_2O$ or a bond;
Q is H, halogen, $CF_3$, $OCF_3$, $CO_2R^2$, $CH_2OR^2$, $CONR^2R^3$ or tetrazol-5-yl;
A is H, halogen, $C_1$-$C_{10}$ alkyl, $C_1$-$C_{10}$ alkyl branched alkyl, or $CO_2R^3$, wherein each $C_1$-$C_{10}$ alkyl, or $C_1$-$C_{10}$ alkyl branched alkyl contains one or more groups selected from the groups consisting of OH, OR and $NR_2$;

B is H, halogen, $C_1$-$C_{10}$ alkyl, or $C_1$-$C_{10}$ alkyl branched alkyl, wherein each $C_1$-$C_{10}$ alkyl, or $C_1$-$C_{10}$ alkyl branched alkyl contains one or more groups selected from the groups consisting of OH, OR and $NR_2$;
R is H or $C_1$-$C_6$ alkyl;
$R^1$ is H, $C_1$-$C_6$ alkyl, $CF_3$, phenyl or biphenyl;
$R^2$ is H, $C_1$-$C_6$ alkyl, C(O)$R^1$ or $SO_2R^1$; and
$R^3$ is H or $C_1$-$C_6$ alkyl.

2. The compound of claim 1, wherein:
X is CH;
Y is $C_1$-$C_3$ alkyl optionally substituted by OH; and
Z is interarylene.

3. The compound of claim 2, wherein Z is phenylene.

4. The compound of claim 2, wherein:
Z is phenylene; and
Q is H, halogen, $CF_3$, $OCF_3$, or $CH_2OCH_3$.

5. The compound of claim 4, wherein Q is $CF_3$.

6. The compound of claim 1, wherein Y is $C_1$-$C_3$ alkyl substituted by OH.

7. The compound of claim 6, wherein Y is CH(OH)$CH_2$.

8. The compound of claim 1, wherein Ar is a 5 membered heteroaryl containing 1 or 2 heteroatoms selected from the group consisting of O, N and S.

9. The compound of claim 1, wherein A is $CO_2R^3$ and B is H.

10. The compound of claim 1, wherein n is 3.

11. The compound of claim 1, wherein:
Ar is a 5 membered heteroaryl containing 1 or 2 heteroatoms selected from the group consisting of O, N and S;
n is 1, 2 or 3;
X is CH;
Y is $C_1$-$C_3$ alkyl optionally substituted by OH; and
Z is interarylene.

12. The compound of claim 1, wherein;
Ar is a 5 membered heteroaryl containing 1 or 2 heteroatoms selected from the group consisting of O, N and S;
n is 1, 2 or 3;
X is CH;
Y is CH(OH)$CH_2$; and
Z is phenylene.

13. The compound of claim 1, wherein:
Ar is a 5 membered heteroaryl containing 1 or 2 heteroatoms selected from the group consisting of O, N and S;
n is 1, 2 or 3;
A is $CO_2R^3$;
B is H;
X is CH;
Y is CH(OH)$CH_2$; and
Z is phenylene.

14. The compound of claim 1, wherein:
Ar is a 5 membered heteroaryl containing 1 or 2 heteroatoms selected from the group consisting of O, N and S;
n is 1, 2 or 3;
A is $CO_2R^3$;
$R^3$ is H;
B is H;
X is CH;
Y is CH(OH)$CH_2$; and
Z is phenylene.

15. The compound of claim 1, wherein:
Ar is a 5 membered heteroaryl containing 1 heteroatom selected from the O and S;
n is 1, 2 or 3;
A is $CO_2R^3$;
B is H;
X is CH;
Y is CH(OH)$CH_2$; and
Z is phenylene.

16. The compound of claim 1, wherein:
Ar is a 5 membered heteroaryl containing 1 heteroatom selected from the O and S;
n is 1, 2 or 3;
A is $CO_2R^3$;
$R^3$ is H;
B is H;
X is CH;
Y is CH(OH)$CH_2$; and
Z is phenylene.

17. The compound of claim 1, wherein:
Ar is a 5 membered heteroaryl containing 1 or 2 heteroatoms selected from the group consisting of O, N and S;
n is 1, 2 or 3;
A is $CO_2R^3$;
$R^3$ is H;
B is H;
X is CH;
Y is CH(OH)$CH_2$;
Z is phenylene; and
Q is $CF_3$.

18. The compound of claim 1, wherein:
Ar is a 5 membered heteroaryl containing 1 heteroatom selected from the O and S;
n is 1, 2 or 3;
A is $CO_2R^3$;
B is H;
X is CH;
Y is CH(OH)$CH_2$;
Z is phenylene; and
Q is $CF_3$.

19. The compound of claim 1, wherein:
Ar is a 5 membered heteroaryl containing 1 heteroatom selected from the O and S;
n is 1, 2 or 3;
A is $CO_2R^3$;
$R^3$ is H;
B is H;
X is CH;
Y is CH(OH)$CH_2$;
Z is phenylene; and
Q is $CF_3$.

20. The compound of claim 1 of the formula:

21. The compound of claim 1 of the formula:

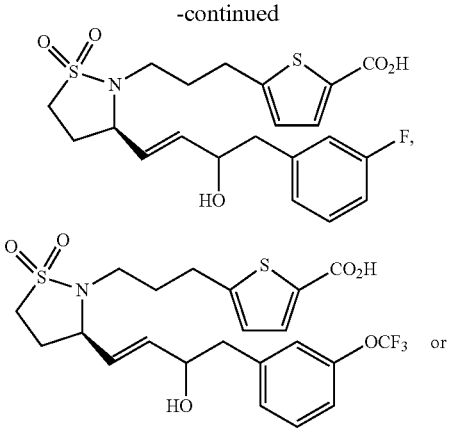
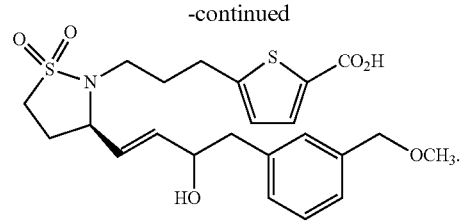
22. A composition comprising a compound according to claim 1, wherein said composition is in an ophthalmically acceptable liquid form.
23. A method for the treatment of glaucoma or ocular hypertension in a subject, the method comprising administering to the subject in need thereof a therapeutically effective amount of a compound or composition of claim 1.
* * * * *